United States Patent [19]

Sawa

[11] Patent Number: 4,735,198
[45] Date of Patent: Apr. 5, 1988

[54] INJURY REDUCTION AND STABILIZING HARNESS

[76] Inventor: Thomas M. Sawa, 2 Jane Street, Suite 511, Toronto, Ontario M6S 4W3, Canada

[21] Appl. No.: 817,890
[22] Filed: Jan. 13, 1986
[51] Int. Cl.$^4$ ............................................. A61F 13/00
[52] U.S. Cl. .................................................... 128/133
[58] Field of Search ...................... 128/87 R, 133, 134, 128/94, DIG. 15; 2/16, 69, 44, 45; 272/135, 137, 139

[56] References Cited

U.S. PATENT DOCUMENTS

| | | | |
|---|---|---|---|
| 1,991,677 | 2/1935 | Jacks | 128/94 |
| 3,920,316 | 7/1976 | Westmoreland, Jr. | 128/134 X |
| 4,480,637 | 11/1984 | Florek | 128/94 |
| 4,589,407 | 5/1986 | Koledin et al. | 128/87 R |
| 4,598,703 | 7/1986 | Lindemann | 128/94 |

Primary Examiner—Robert E. Bagwill
Assistant Examiner—Danton D. DeMille

[57] ABSTRACT

The present invention provides a body harness, particularly suitable for use by athletes, and the like, in either protecting against, or nursing injuries, while still being able to compete in their particular sport. The harness of the present arrangement comprises a first torso fitting portion and a second appendage fitting portion having a secured end at the torso fitting portion and a free end allowing mobility of the appendage to which the second portion is fitted. The harness further includes at least one elasticized strap for extending across from the first to the second portion to control such mobility with a releasable securing means being provided for securing the elasticized strap to both the first and second harness portions.

1 Claim, 3 Drawing Sheets

INJURY REDUCTION AND STABILIZING HARNESS

FIELD OF THE INVENTION

The present invention provides a body harness for use by athletes, and the like, for reducing the likelihood or nursing sports injuries, while allowing the athlete to continue to compete in his or her particular sport.

BACKGROUND OF THE INVENTION

There are often times when an athlete sustains an injury which is not severe enough to justify discontinuing the sport until the injury is healed but which is extremely painful and which is susceptible, if continuing to play the sport, to more serious injury.

According to conventional practice, athletes are taped against further injury, and although taping is the best answer to date to guard against further serious injury, this taping still has very substantial drawbacks. Firstly, there is quite an art to taping and only experienced trainers, doctors, etc. are generally capable of applying a good tape job. In cases where an injury is sustained in an area inaccessible to the athlete, such as the shoulder region, it is difficult, if not impossible, for the athlete to provide a self-taping job.

Further drawbacks relating to conventional taping practice include the fact that often large amounts of tape are required which is not reuseable and therefore very costly. In addition, the removal of the tape which is generally applied to the skin's surface, is extremely painful.

In addition to all of the above problems, probably the most objectionable drawback, with respect to taping is that initially it is extremely restrictive in terms of amount of movement allowed by the taping job; however, over time, i.e. the time during which the athlete is competing, the taping job tends to stretch and not being of an elasticized nature, loses its effectiveness, which results in the requirement of further taping, as we often see while watching a football game, where the football player is being retaped at the sidelines, while the game is being played.

SUMMARY OF THE PRESENT INVENTION

The present invention provides a body harness, or harness arrangement, which is particularly designed to overcome all of the objections raised above with respect to conventional taping practice. More specifically, the harness arrangement of the present invention comprises a first torso fitting portion and a second appendage fitting portion, having a secured end at the first portion and a free end allowing mobility of the appendage to which the second portion is fitted. Further provided with the arrangement is at least one elasticized strap for extending across from the first to the second portion to control such mobility and releasable securing means for securing the elasticized strap to both the first and the second portions.

In a preferred embodiment of the present invention the harness arrangement is particularly designed for use in reducing the likelihood or the healing of shoulder injuries, with the first torso fitting portion being fitted around the chest area and providing a support base for the second appendage fitting portion, which is fitted around the upper arm with the elasticized strap extending from the chest region to the upper arm region. The elasticized strap extending across from the first to the second harness portion allows movement of the upper arm and shoulder region, but, due to its elasticity, tends to fight against and therefore control such movement. In a further preferred embodiment, a number of elasticized straps are provided extending from the first harness portion to different locations on the second harness portion of adding further control to the movement of the appendage.

BRIEF DISCUSSION OF THE DRAWINGS

The above, as well as other advantages and features of the present invention will be described in greater detail according to the preferred embodiments of the present invention in which.

DETAILED DESCRIPTION ACCORDING TO THE PREFERRED EMBODIMENTS OF THE PRESENT INVENTION

Figure 1:
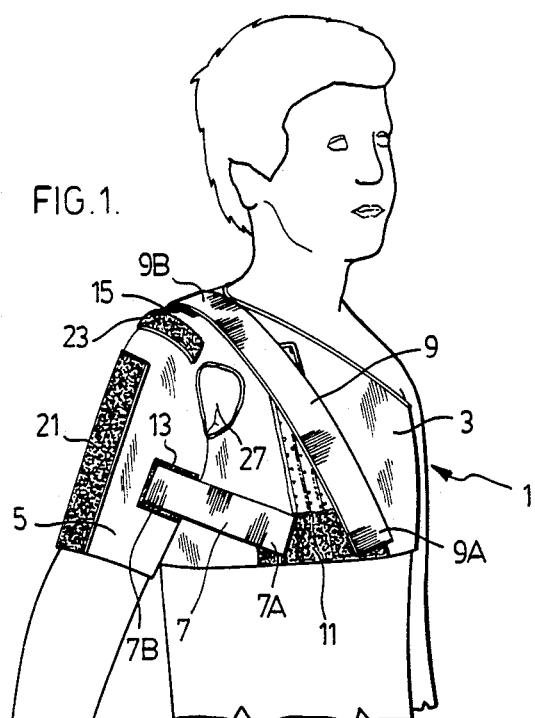
FIG. 1 is a front perspective view showing the fitting of a harness arrangement according to a preferred embodiment of the present invention.
Figure 2:
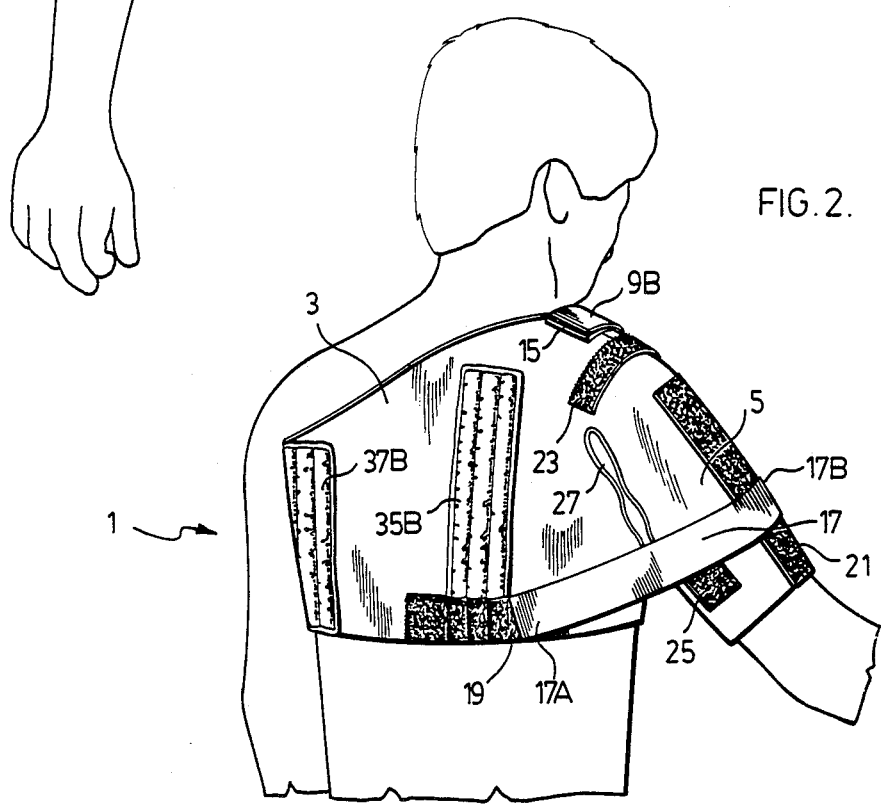
FIG. 2 is a rear perspective view of the harness arrangement of FIG. 1.

FIGS. 1 and 2 show a shoulder harness arrangement, generally indicated at 1 and including a first torso or chest fitting portion 3, and a second appendage or arm fitting portion 5, which is integrally secured at its upper end to the torso fitting portion. The lower end of the appendage, or arm fitting portion, is free to enable movement of the arm relative to the chest or torso.

Figure 3:
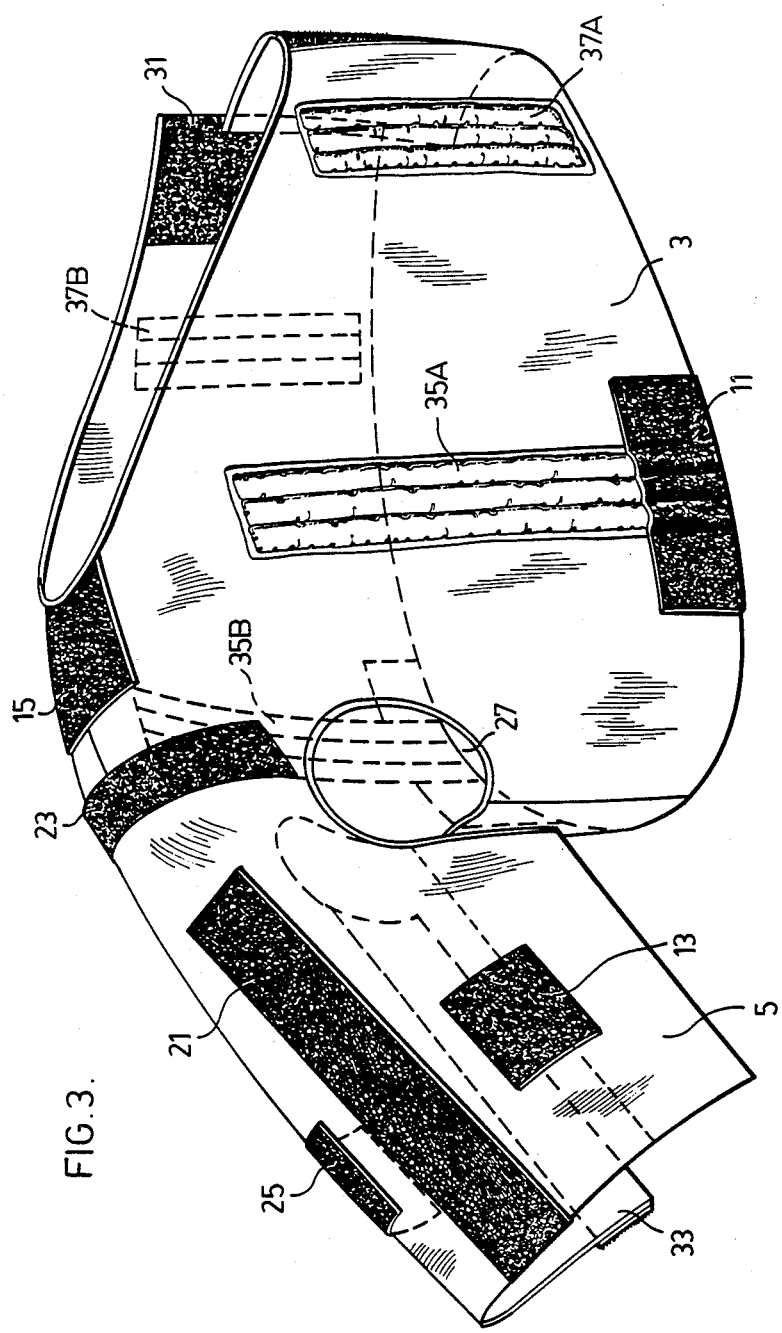
FIG. 3 is a further enlarged perspective view of the harness arrangement of FIGS. 1 and 2.

Referring to FIG. 3, each of the first and second harness portions is constructed from an elasticized material, with the first torso fitting portion including a VELCRO ™ closure 31, and the second, or appendage fitting portion including a VELCRO ™ closure 33. This combination of a VELCRO ™ closure with expandable material, enables the harness to be quickly and easily secured in position as shown in FIGS. 1 and 2, with the capability of accommodating many different body shapes and sizes.

Provided on the first torso fitting portion are a plurality of stabilizer bars, or strips shown at 35A, 35B, 37A and 37B. These stabilizer strips ensure that the torso portion of the harness, once fitted in position provides an extremely effective stabilizing base for controlling movement of the appendage, or arm fitting portion, as will be described later in detail. It is to be noted that the torso fitting portion of the harness is shaped such that the VELCRO ™ closure side runs down beneath the left arm, or the arm on the opposite side from the appendage fitting portion, leaving complete mobility of the left arm. At the right arm side, or the side of the appendage fitting portion, the harness includes a cut out region 27, extending from the front to the back of the harness, as can be seen in FIGS. 1 and 2, so that there is no chafing at the armpit region, as the fitted arm is moved up and down with the harness in position.

It is to be appreciated from the description thus far that not only is the individual able to self-fit the harness, but is also able to self-release the harness which is reuseable for future occasions. In addition, the elasticized material of the first and second harness portions in itself provides both stabilizing and heating effects, which are particularly desireable, in the case of mending or healing an injury.

As mentioned above, the appendage portion, other than at its secured end to the torso portion, allows mobility of the arm and shoulder. However, as a mobility control feature, i.e. to control against excessive degrees of elevation and abduction of the shoulder region, a plurality of elasticized straps are provided which, once fitted in position, extend across from the support torso portion to the moveable appendage portion. It is to be appreciated that the elasticized straps still allow movement of the arm and shoulder, but act in a restricting or restraining manner, which is particularly helpful in the case of sudden and abrupt movements of the arm and shoulder, where the straps immediately provide a pulling resistance against excessive movements. Due to the elasticity of the straps, they can be stretched an infinite number of times while still maintaining their elastic properties.

The particular arrangement shown in FIGS. 1 and 2 includes straps 7 and 9 at the front of the harness, and strap 17 at the rear of the harness. Each of these straps, as mentioned above, includes an elasticized body portion, and is additionally provided with VELCRO TM end regions. In cooperation with the VELCRO TM end regions on the straps, each of the torso and appendage fitting portions of the harness includes VELCRO TM securing regions for securing of the straps between the two harness portions.

As will be clearly seen in FIGS. 1 and 2, the elasticized straps are of varying lengths, with strap 7 extending from the lower portion of the torso fitting portion to about the mid-region of the appendage fitting portion. Here it will be seen that the torso fitting portion includes a VELCRO TM strip 11, for receiving end portion 7A of strap 7, while the appendage fitting portion includes a VELCRO TM strip 13, for receiving the end portion 7B, of elasticized strip 7. The other strap at the front of the harness, i.e. strap 9, is also secured at its one end 9A from VELCRO TM strip 11, which is of an extended length for receiving more than one elasticized strap, with the other end 9B of strap 9 being secured to a further VELCRO TM securing region 15. This latter strap extends from the top to the bottom of the harness and therefore is of an increased length, relative to strap 7. Strap 17 at the back of the harness is of even greater length for extending from its one VELCRO TM end 17A, secured to VELCRO TM strip 19, at the back of the torso portion of the harness, to the appendage portion of the harness where VELCRO TM end 17B, of strap 17 is secured to a further VELCRO TM securing strip 21, provided directly on the appendage portion of the harness.

With each of the straps fitted in position, as shown in FIGS. 1 and 2, the individual is still capable of moving the arm and shoulder region, but the suddenness and the amount of the movement is restricted to a point where there is a substantial reduction in the likelihood of incurring an injury or aggravating any existing injury. Accordingly, athletes such as hockey players, and the like, when wearing the harness arrangement, according to the present invention, are capable of playing with injuries, where in the past such injuries might well have sidelined them, without the use of the harness.

Figure 4:
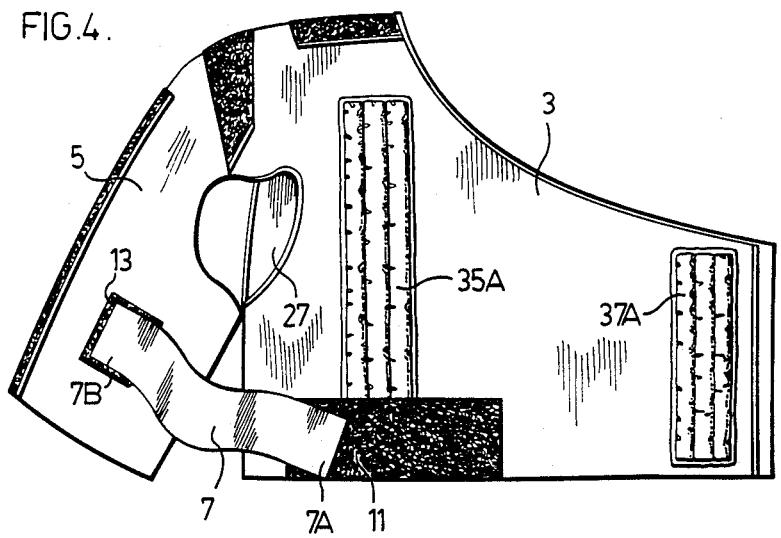
FIG. 4 is a front plan view of the harness arrangement of FIG. 3 in a relaxed position.
Figure 5:
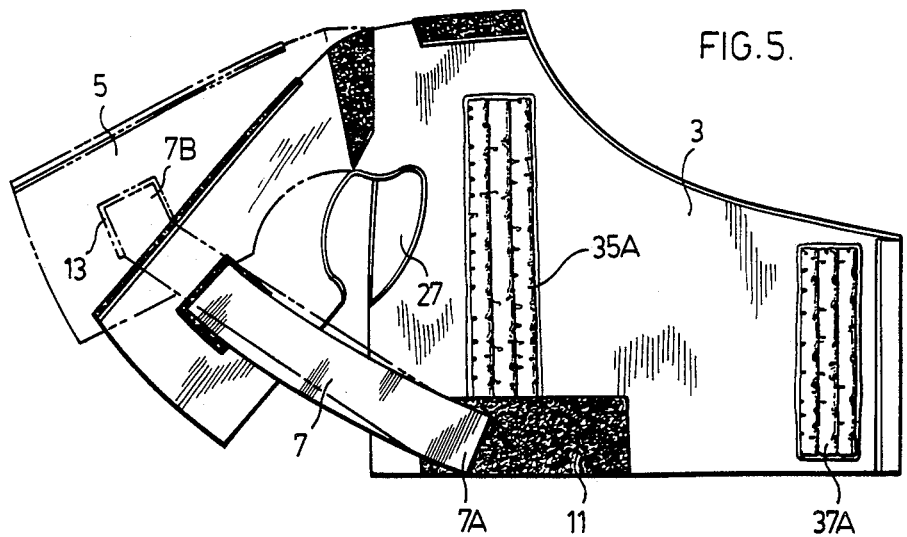
FIG. 5 is a view similar to FIG. 4 showing the controlling action of the elasticized strap from the first to the second harness portion.

FIGS. 4 and 5, clearly demonstrate the principal of the present invention. Here it will be seen that in the relatively relaxed position of FIG. 4, there is essentially complete mobility of the arm and shoulder region, whereas in FIG. 5, although the arm is able to move to a more elevated position, strap 7 has a tendency to restrict such movement. Furthermore, the greater the movement the more the restriction provided by strap 7, which increases in its pulling action back to the FIG. 4 relaxed position, with greater elevation of the arm. Strap 7 would also have the effect of restricting any rearward abduction of the shoulder, while strap 17 would limit the forward movement of the shoulder.

The harness, as shown in the drawings, includes further VELCRO TM securing regions, such as VELCRO TM strip 23, running around the outside of the shoulder joint. The provision of these numerous VELCRO TM securing regions enables the straps to be secured at many different positions from the torso to the appendage fitting portion, according to the direction and degree of control required through the elasticized straps.

One particularly desireable feature regarding the stabilizing bars, or strips, is that each of these bars or strips is bendable, to ensure proper fitting of the harness and is resistant to compression and expansion, further adding to the support or stabilizing influence of the torso fitting portion of the harness.

The drawings and the description above relate to a shoulder fitting harness; however, it is to be appreciated that the same principals would apply to a harness for supporting other regions of the body, such as a hip area, to guard against hip and upper leg injuries. Again, the harness would include a torso fitting portion, which in this instance, would fit around the waist region, and an appendage fitting portion, which would fit around the upper leg area, for supporting the upper leg and the hip region.

Although various preferred embodiments of the present invention have been described herein in detail, it will be appreciated by those skilled in the art, that variations may be made thereto without departing from the spirit of the invention or the scope of the appended claims.

The embodiment of the invention in which exclusive property or privilege is claimed are defined as follows:

1. A shoulder harness arrangement for stabilizing while allowing controlled movement of an injured shoulder, said harness arrangement comprising a first chest fitting portion having a shoulder mounting region and a second upper arm fitting portion having a secured end at said shoulder mounting region, a free end outwardly from said secured end and an underarm cut-out region therebeneath for allowing mobility without chafing of an upper arm to which said second upper arm fitting portion is fitted, said shoulder harness including a plurality of extended length velcro securing areas providing different attachment locations at both said first chest fitting portion and said second upper arm fitting portion and further including a plurality of elasticized straps for extending between said securing areas restricting the amount of movement allowed to the injured arm.

* * * * *